United States Patent [19]
DeMali

[11] Patent Number: 5,894,095
[45] Date of Patent: Apr. 13, 1999

[54] MIXING DRILL WITH SPEED SENSING WITH MULTIPLE PRESET SPEEDS

[76] Inventor: Gary W. DeMali, 2569 Saxe Rd., Mogadore, Ohio 44260

[21] Appl. No.: 08/842,907

[22] Filed: Apr. 17, 1997

[51] Int. Cl.$^6$ ........................................ G01D 9/00
[52] U.S. Cl. ........................ 73/862.27; 73/862.193
[58] Field of Search ................... 73/862.193, 862.23, 73/862.51, 862.27, 862.381, 54.35; 366/142

[56] References Cited

U.S. PATENT DOCUMENTS

| | | | |
|---|---|---|---|
| 3,898,563 | 8/1975 | Erisman | 324/166 |
| 4,120,051 | 10/1978 | Lohning | 366/142 |
| 4,352,063 | 9/1982 | Jones et al. | 324/171 |
| 4,410,846 | 10/1983 | Gerber et al. | 318/490 |
| 4,484,468 | 11/1984 | Gau et al. | 773/54.35 |
| 4,540,318 | 9/1985 | Hornung et al. | 408/9 |
| 4,771,223 | 9/1988 | Armstrong et al. | 318/314 |
| 4,901,587 | 2/1990 | Deremo et al. | 73/862.06 |
| 5,014,793 | 5/1991 | Germanton et al. | 73/862.22 |
| 5,544,534 | 8/1996 | Fujitaka | 73/862.23 |
| 5,563,482 | 10/1996 | Shaw et al. | 73/862.23 |
| 5,567,886 | 10/1996 | Kettner | 73/862.23 |

*Primary Examiner*—Max H. Noori

[57] ABSTRACT

A new mixing drill with speed sensing with multiple preset speeds for providing a display of drill motor speed while mixing for indicating the viscosity of drywall joint compound and plaster mixtures and providing a quick and easy method of mixing drywall compound to a specific consistency. The inventive device includes an electric drill, an on off switch, a detachable drill bit with vanes, a drill chuck with a magnetic marker, a magnetic sensor attached to the drill body, a drill speed counter, a motor controller, a keypad, a micro controller and a digital LCD display for displaying drill target speed setting and alternatively displaying the actual speed to target speed ratio for indicating viscosity of a mixture. After the mixing drill with speed sensing is has a target speed setting and the drill is started mixing, the mixing drill with speed sensing operates according to a control program such that pressing a keystroke initiates a control subroutine such that when the motor moves the vaned drill bit in a viscous mixture of materials and the viscosity of the mixture reduces with increased mixing time and motor speed increases with increased mixing time the motor will continue to mix until the sensed motor speed reaches the target speed at which time the motor controller serially connected to the on off switch and the drill motor stops the motor and mixing is finished.

12 Claims, 3 Drawing Sheets

PREFILL AND FIRST COAT

| 1 | 2 | 3 |

FINISH COAT AND HAND TAPING

| 4 | 5 | 6 |

TOOL TAPING AND TEXTURING

| 7 | 8 | 9 |

| * | 0 | # |

5,894,095

1

MIXING DRILL WITH SPEED SENSING WITH MULTIPLE PRESET SPEEDS

BACKGROUND OF THE INVENTION

1. Field of the Invention

The present invention relates to motor speed monitoring and control systems and more particularly pertains to a new mixing drill with speed sensingwith multiple preset speeds for providing a display of drill motor speed while mixing for indicating the viscosity of drywall joint compound and plaster mixtures and providing a quick and easy method of mixing drywall compound to a specific consistency.

2. Description of the Prior Art

The use of motor speed monitoring and control systems is known in the prior art. More specifically, motor speed monitoring and control systems heretofore devised and utilized are known to consist basically of familiar, expected and obvious structural configurations, notwithstanding the myriad of designs encompassed by the crowded prior art which have been developed for the fulfillment of countless objectives and requirements.

Known prior art motor speed monitoring and control systems include U.S. Pat. No. 4,771,223 Armstrong et al; U.S. Pat. No. 4,901,587 Deremo et al; and monitoring of speed of rotation in well drilling U.S. Pat. No. 5,305,836 Hollbrook et al. Elements used in a novel combination in the mixing drill with speed sensing with multiple preset speeds are known prior art magnetic speed sensors in bicycle speedometer/odometers seen in U.S. Pat. No. 4,352,063 Jones et al and U.S. Pat. No. 3,898,563 Erisman; prior art actuation of a drill under control of a microcomputer seen in U.S. Pat. No. 5,181,808 Griggs et al; and prior art transmitting information from the head of a drill rod in mining operations in U.S. Pat. No. 5,268,683 Stolarczyk.

While these devices fulfill their respective, particular objectives and requirements, the aforementioned patents do not disclose a new mixing drill with speed sensing with multiple preset speeds. The inventive device includes an electric drill, an on off switch, a detachable drill bit with vanes, a drill chuck with a magnetic marker, a magnetic sensor attached to the drill body, a drill speed counter, a motor controller, a keypad, a microcontroller and a digital LCD display for displaying drill target speed setting and alternatively displaying the actual speed to target speed ratio for indicating the viscosity of a mixture.

In these respects, the mixing drill with speed sensing with multiple preset speeds according to the present invention substantially departs from the conventional concepts and designs of the prior art, and in so doing provides an apparatus primarily developed for the purpose of providing a display of drill motor speed while mixing for indicating the viscosity of drywall joint compound and plaster mixtures and providing a quick and easy method of mixing drywall compound to a specific consistency.

SUMMARY OF THE INVENTION

In view of the foregoing disadvantages inherent in the known types of motor speed monitoring and control systems now present in the prior art, the present invention provides a new mixing drill with speed sensing with multiple preset speeds construction wherein the same can be utilized for providing a display of drill motor speed while mixing for indicating the viscosity of drywall joint compound and plaster mixtures and providing a quick and easy method of mixing drywall compound to a specific consistency.

2

The general purpose of the present invention, which will be described subsequently in greater detail, is to provide a new mixing drill with speed sensingwith multiple preset speeds apparatus and method which has many of the advantages of the motor speed monitoring and control systems mentioned heretofore and many novel features that result in a new mixing drill with speed sensing with multiple preset speeds which is not anticipated, rendered obvious, suggested, or even implied by any of the prior art motor speed monitoring and control systems, either alone or in any combination thereof.

To attain this, the present invention generally comprises an electric drill, an on off switch, a detachable drill bit with vanes, a drill chuck with a magnetic marker, a magnetic sensor attached to the drill body, a drill speed counter, a motor controller, a keypad, a micro controller and a digital LCD display for displaying drill target speed setting and alternatively displaying the actual speed to target speed ratio for indicating viscosity of a mixture.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new mixing drill with speed sensing with multiple preset speeds apparatus and method which has many of the advantages of the motor speed monitoring and control systems mentioned heretofore and many novel features that result in a new mixing drill with speed sensing with multiple preset speeds which is not anticipated, rendered obvious, suggested, or even implied by any of the prior art motor speed monitoring and control systems, either alone or in any combination thereof.

It is another object of the present invention to provide a new mixing drill with speed sensing with multiple preset speeds which may be easily and efficiently manufactured and marketed.

It is a further object of the present invention to provide a new mixing drill with speed sensing with multiple preset speeds which is of a durable and reliable construction.

An even further object of the present invention is to provide a new mixing drill with speed sensing with multiple preset speeds which is susceptible of a low cost of manufacture with regard to both materials and labor, and which accordingly is then susceptible of low prices of sale to the consuming public, thereby making such mixing drill with speed sensing with multiple preset speeds economically available to the buying public.

Still yet another object of the present invention is to provide a new mixing drill with speed sensing with multiple preset speeds which provides in the apparatuses and methods of the prior art some of the advantages thereof, while simultaneously overcoming some of the disadvantages normally associated therewith.

Still another object of the present invention is to provide a new mixing drill with speed sensing with multiple preset speeds for providing a display of drill motor speed while mixing for indicating the viscosity of drywall joint compound and plaster mixtures and providing a quick and easy method of mixing drywall compound to a specific consistency.

Yet another object of the present invention is to provide a new mixing drill with speed sensing with multiple preset speeds which includes an electric drill with a multispeed selection switch, an on off switch, a detachable drill bit with vanes, a drill chuck with a magnetic marker, a magnetic sensor attached to the drill body, a drill speed counter, a motor speed controller, a keypad, a micro controller and a digital LCD display for displaying drill target speed setting and alternatively displaying the actual speed to target speed ratio for indicating viscosity of a mixture.

Still yet another object of the present invention is to provide a new mixing drill with speed sensing that continuously monitors the rpm of the motor and displays ratio of preset speed to actual speed for quantitatively describing the viscosity of a mixture of drywall compounds. In a method for use, the target speed is preset based on the viscosity needed for a desired type of mixture. The target speed is set for the final desired viscosity, initially a slower actual speed is monitored as more viscous materials begin to mix displaying a lower speed on the display and alternatively displaying a ratio of target speed to desired speed. As the process of mixing continues the viscosity is reduced and the speed increases. The actual sensed speed to preset speed ratio changes concomitantly as the speed of the drill increases. The ratio reaches 100 percent of the target speed at which point drywall joint compound is finished mixing, and the mixing drill with speed sensing with multiple preset speeds will optionally stop mixing and the compound is prepared consistently from batch to batch. The described method results in improved quality of prepared materials because the mixing drill with speed sensing with multiple preset speeds apparatus provides accuracy, convenience and ease of operation for the user.

Even still another object of the present invention is to provide a new mixing drill with speed sensing that has multiple preset speed for various mixture consistencies required in mixing dry wall compound and plastering materials.

Even still another object of the present invention is to provide a new mixing drill with speed sensing that has programmable preset speeds allowing changes to be made in the preset target speeds for multiple modes for mixing a wide variety of materials.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
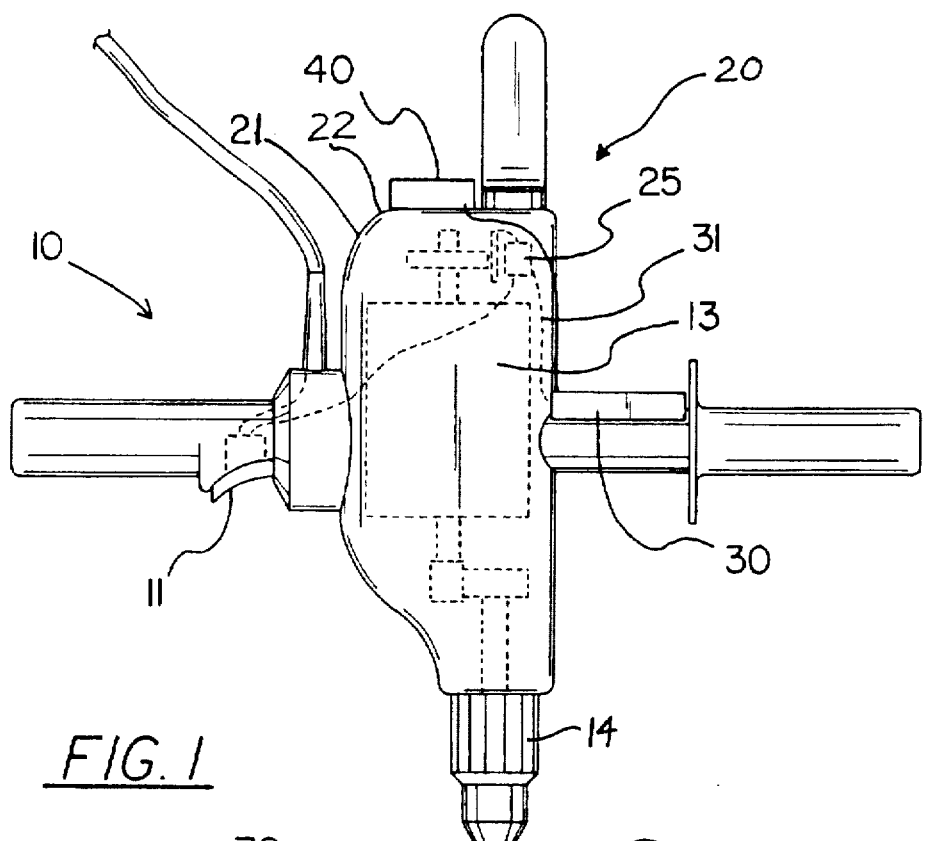
FIG. 1 is a partially exploded right side view of a new mixing drill with speed sensing with multiple preset speeds according to the present invention.
Figure 2:
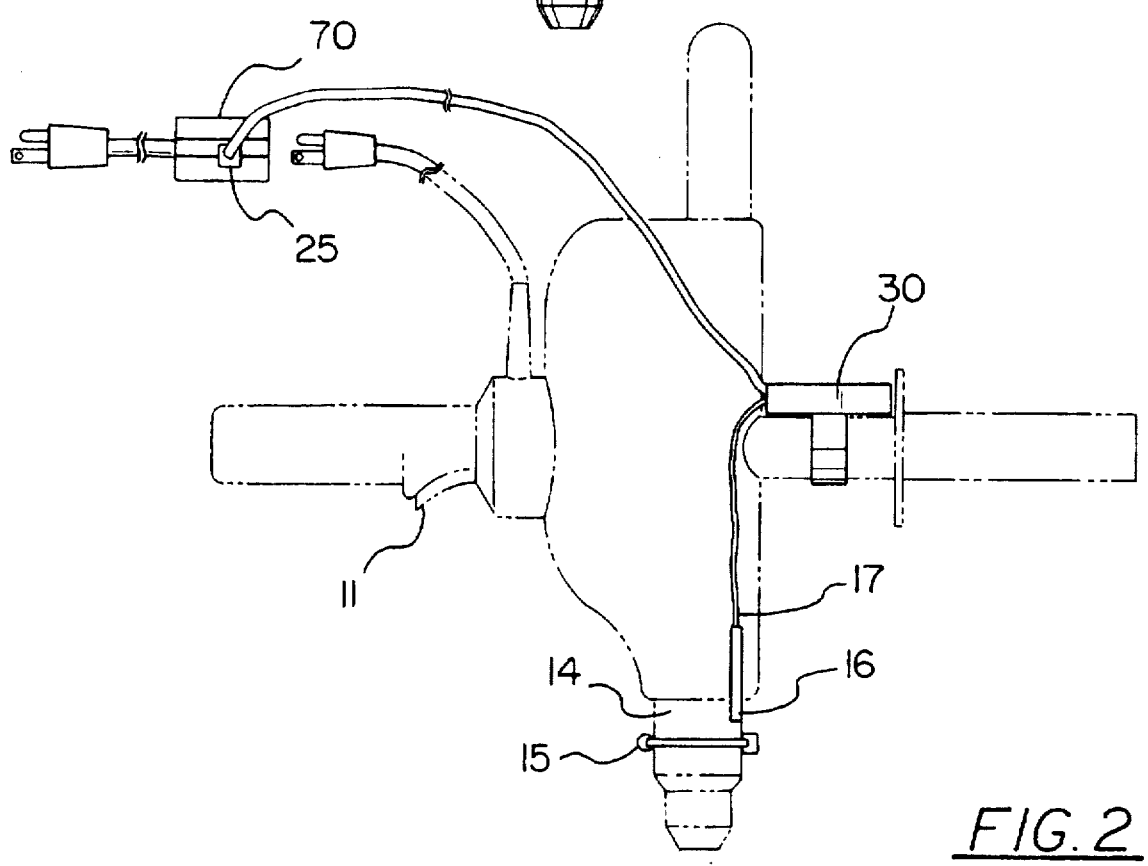
FIG. 2 is a right side elevation view of the motor speed sensor and LCD display
Figure 3:
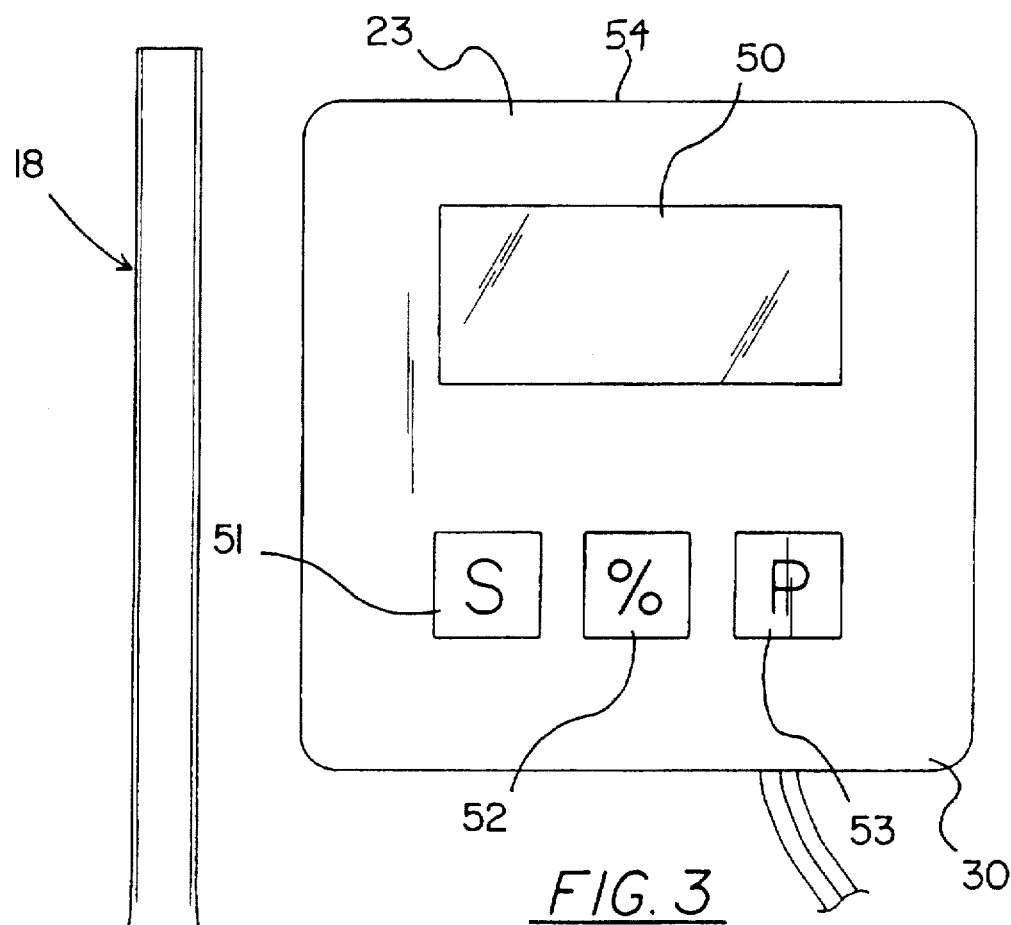
FIG. 3 is a view of the display of the present invention.
Figure 4:
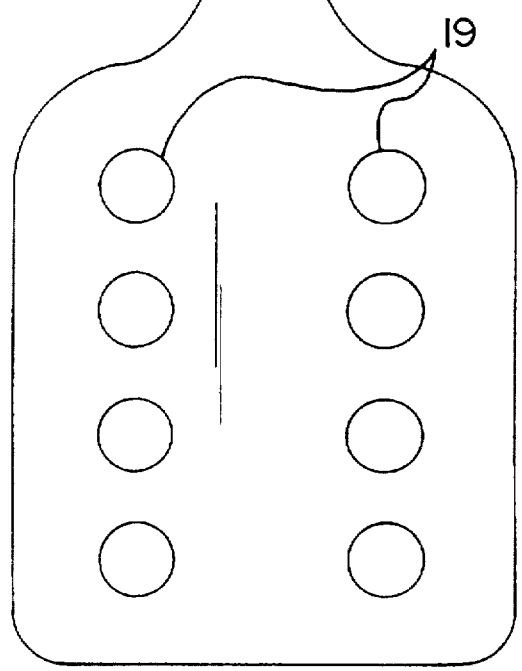
FIG. 4 is a side view of the drill bit with mixing vanes of the invention.
Figures 5, 6:
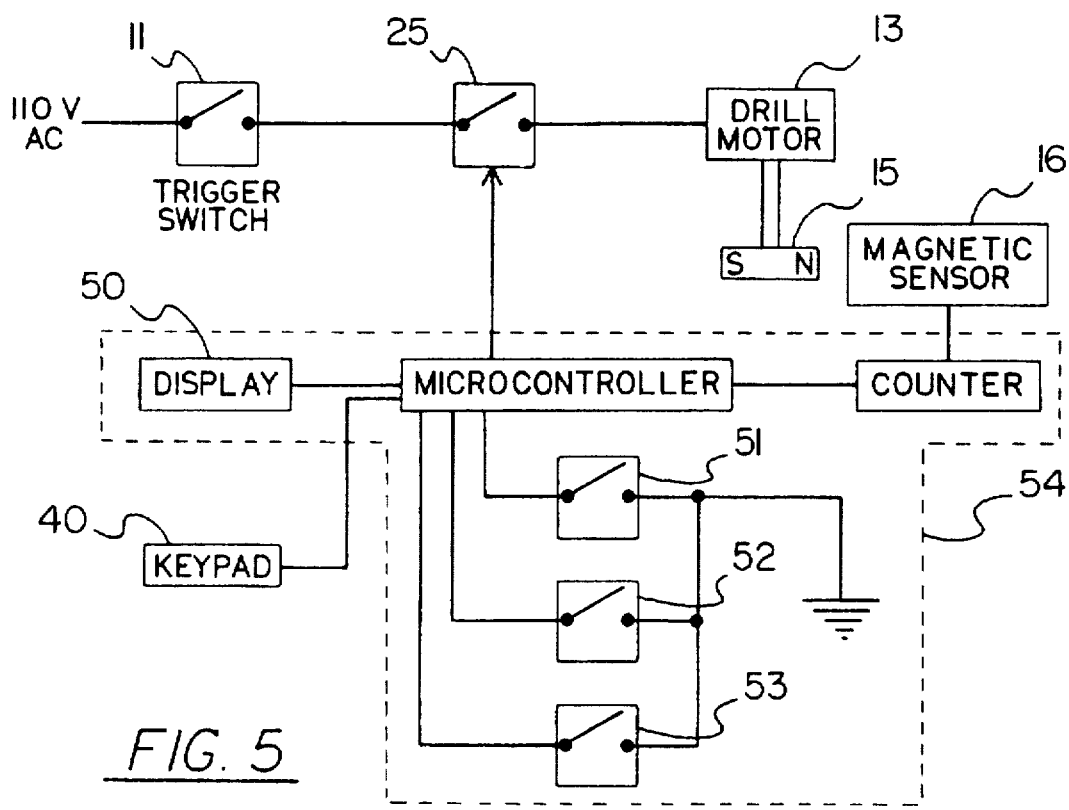
FIG. 5 is an electrical block diagram of the present invention.
FIG. 6 is a view of numeric keypad labeled for three settings in each of three mixing modes 1 2 3 for prefill and first coat, 4 5 6 for finish coat and hand taping, and 7 8 9 for tool taping and texturing.

With reference now to the drawings, and in particular to FIGS. 1 through 6 thereof, a new mixing drill with speed sensing with multiple preset target speeds embodying the principles and concepts of the present invention and generally designated by the reference numeral 10 will be described.

As best illustrated in FIGS. 1 through 6, the mixing drill with speed sensing with multiple preset target speeds 10 comprises a large single speed electric drill 20, an on off switch 11, a detachable drill bit 18 with drill bit vanes 19, a drill rotor chuck 14 with an attached magnetic marker 15, a magnetic sensor 16 attached to the forward portion 24 of the drill body 21, a sensor wire 17 connecting the magnetic sensor to a drill speed counter 23, a motor speed controller 12 with an on off function is connected by control signal wires 30 to a programmable microcontroller 30. Mounted on the rearhand portion 22 of the drill body 21 is a small phone style numeric keypad 40. The programmable microcontroller 30 and operates independently of the drill speed counter 23. The LCD display 50 is driven by both the drill speed counter 23 and the programmable microcontroller 30 and both are located in the LCD display housing 54. The LCD displays drill target speed setting obtained from the microcontroller 30 after a first display push button 51 is pressed and alternatively displays the actual speed obtained from the drill speed counter 23 indicating the viscosity of a mixture after a second display push button 52 is pressed and alternatively displays the ratio of actual speed to target speed ratio obtained from the microcontroller 30 indicating the completeness of mixing after a third display push button 53 is pressed.

The trigger switch 11 turns the drill motor 13 off and on The trigger switch is serially connected with the a motor control controller with an on/off contact 12 that is receives on off signals from a microcontroller 30. The drill speed counter 23 calculates the actual speed of the motor 13 and sends the speed data to the LCD display 50 and to the microcontroller 30 which monitors the speeds the motor reaches during the mixing process. The microcontroller 30 calculates the ratios of actual speed to target speeds during the mixing process for display on the LCD and uses the motor speed data for control purposes. The mixing drill with speed sensing with multiple preset speeds is optionally programmed to stop when the speed reaches the target speed. The microcontroller 30 uses preprogrammed target speeds in one embodiment of the invention and in another embodiment the target speed is preprogrammed is to target speeds particularly chosen for a combination of drill bit with mixing vanes and drill motor.

In use, the user first enters the rated RPM of the drill on the compact numeric keypad 40 attached on the rearhand portion 22 of the drill body 21 on which the invention is being installed. The user installs the magnet 15 on the drill chuck and the magnetic sensor on the front housing of the drill body. The motor speed LCD display is mounted rearfacing on the lower portion of the upper extension handle 61 of the drill. An external lead connected to the magnetic sensor is attached to the drill body and connected to the display. The user turns on the counter, runs the drill and views the tachometer display to check the drill speed at no load. The user compares the maximum speed with the programmed maximum speed by checking the speed on the LCD readout. The drill has a characteristic speed versus load curve that is used to monitor the consistency of the mixture. A preprogrammed setting for a particular drill, paddle and mixture would avoid the requirement of the programming of a target speed for each of the settings described below. However, a microcontroller measurement system is capable of being programmed to stop mixing at several preset speeds at which the desired consistency is reached. In the example below nine preset target speeds are preprogrammed for use in nine typical drywall mud mixing operations.

The user then enters the desired consistency of the final mixed product. The available choices are 1, 2 and 3 for various consistencies of prefill or first coat, 2, 4, and 5 for various consistencies for material to be used as a finish coat, and 7, 8 and 9 for material do be used mechanized taping or texturing. The drill is turned on and set into the mixture. The display is set to monitor the ratio of actual RPM to target RPM. The ratio quantitatively describes the viscosity of the materials being mixed. The invention monitors the speed of the drill. Specifically, the more viscous the material the slower the actual speed and the lower the observes and calculated speed ratio. Since the machine speed gradually increases as the viscosity is reduced during mixing the ratio can be used to determine when to stop mixing. When the ratio reaches the previously entered setting and the ratio reaches 100% the information is displayed and optionally the drill control may be set to shutoff when the target speed is reached.

Another preferred embodiment is an off the shelf mixing appliance that has preprogrammed target speed settings for each mixing mode preprogrammed within the microcontroller system so that programming of maximum speed and target speeds for each setting is not necessary. Mass production cost is reduced using ROM programmed microcontroller chips. More consistent mixing results can be achieved using pre-tested paired combinations of target speed, drill motor size and selected vaned drill bits.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A mixing drill with speed sensing with multiple preset speeds comprising:

an electric drill having a housing;

a drill motor positioned in the housing;

an on off switch means for turning said drill on and off;

a motor speed sensing means for sensing the motor speed;

a motor control means for controlling the operation of the drill motor, the motor control means being connected to the on off switch and the motor speed sensing means such that the motor control means shuts off the drill motor when a selected predetermined motor speed is reached;

a microcontroller connected to a keypad and the motor control means, the microcontroller being for selectively choosing the predetermined speed at which the motor control means shuts off the drill motor;

signal means connecting the microcontroller to a display means for showing a target motor speed;

a first selector means for controlling the display means by such control method that causes the LCD to display the target motor speed;

a second selector means for controlling the display means by such control method that causes the LCD to display an actual motor speed;

a third selector means for controlling the display means by such control method that causes the LCD to display the ratio of actual speed to target speed as calculated by the microcontroller; and a removable drill bit with drill bit vanes.

2. The mixing drill with speed sensing with multiple preset speeds of claim 1, wherein the motor speed sensing means comprises a magnet means on a rotor chuck and a magnet sensor means attached to the housing.

3. The mixing drill with speed sensing with multiple preset speeds of claim 1, wherein the means for counting the motor speed comprises a motor speed counter connected to the means for sensing the sensed motor speed.

4. The mixing drill with speed sensing with multiple preset speeds of claim 1, wherein the microcontroller is capable of storing speeds input from the keypad means for displaying a target speed ratio by calculating and displaying the ratio of sensed speed obtained from the drill speed counter to a target speed input through the keypad.

5. The mixing drill with speed sensing with multiple preset speeds of claim 1 wherein the keypad is a numeric keypad and wherein the microcontroller is connected to the numeric keypad and to the drill speed counter and wherein the microcontroller follows a method for recording a maximum motor speed according to the steps of: first, pressing a display push button, second, running the drill without the drill bit or other load for short time and third while drill speed is at a stabilized maximum speed pressing a special function key on the numeric keypad recording the measured maximum motor speed.

6. The mixing drill with speed sensing with multiple preset speeds of claim 1, wherein the keypad is a numeric keypad and wherein the microcontroller connected to the numeric keypad and to the drill speed counter and wherein the microcontroller follows a method for recording a maximum motor speed according to the steps of: first, pressing a display push button, second, pressing a special function key on the numeric keypad, third, digitally entering maximum speed, and fourth pressing a special function key on the numeric keypad storing the digitally input maximum speed.

7. The mixing drill with speed sensing with multiple preset speeds of claim 1, wherein the keypad is a numeric keypad and wherein the microcontroller connected to the numeric keypad and the motor control means is programmable to allow programmable input of multiple target speeds through entry on the numeric keypad and wherein the program control method comprises storing a mode number and storing a target speed associated with the mode number, and wherein the drill motor is started by pressing a mode selection key, entering a mode number then starting the drill motor.

8. The mixing drill with speed sensing with multiple preset speeds of claim 5, wherein the step of the program control method which stores a target speed comprises the steps of pressing a mode key on the keypad and entering by digital input a mode number, followed by the steps of entering a target speed by digital input of a target speed number and finally by pressing the mode key, storing the entered speed and mode, and wherein multiple modes and associated speeds are recorded.

9. The mixing drill with speed sensing with multiple preset speeds of claim 1, wherein the keypad is a numeric keypad and wherein the microcontroller is connected to the numeric keypad and the microcontroller has an indexed lookup array table with stored mode and preset speed data in preprogrammed data structure and the microcontroller is programmable to allow retrieval of input of multiple target speeds stored in the lookup table through entry on the numeric keypad of an index number and wherein the program control method comprises pressing a key sequence and entering an index number, pressing a second special key and causing the microcontroller to complete the operation of sequentially storing a preprogrammed set of mode and target speed associated with the mode number for immediate use in the mixing drill with speed sensing with multiple preset speeds.

10. The mixing drill with speed sensing with multiple preset speeds of claim 1, wherein the keypad is a numeric keypad and wherein the microcontroller connected to a keypad and the motor control means is programmed to accomplish a set target speed operation by allowing reading and displaying of a preprogrammed target speeds through entry of a mode number on the numeric keypad and wherein the program control method comprises entering a mode number, displaying the target speed and pressing a unique key associated with the set target speed operation.

11. The mixing drill with speed sensing with multiple preset speeds of claim 10, wherein the program control method is such that the drill is started and a keystroke sequence is used to initiate a control program that allows the drill to operate until the speed reaches the preprogrammed target speed.

12. A mixing drill for mixing dry mixing material with a liquid to consistently produce a mixture of a desired viscosity, the mixing drill comprising:

a drill housing;

a drill motor within the drill housing, said drill motor being adapted for providing a consistent amount of power for rotating a mixing bit whereby variations in the motor speed and thereby the rotational speed of the mixing bit are due to changes in viscosity of the mixture;

a tachometer being for indicating the drill motor speed;

a motor control means for controlling the operation of the drill motor, the motor control means being connected to a power switch and a motor speed sensing means such that the motor control means cuts off power to the drill motor when a selected predetermined motor speed is reached;

a motor power selection means for choosing a desired motor power such that the motor will provide a consistent selected amount of power for rotating said mixing bit;

a display for indicating the tachometer readout, selected motor power level, and a selected motor shut off speed; and a selector means for causing the display to display a ratio of the ratio of the drill motor speed sensed by the tachometer and the selected predetermined motor speed;

wherein the motor power selection means includes a keypad having a number of keys, each of said number of keys having an associated motor speed, said keypad being connected to said drill motor such that a desired motor power level is selected by pressing the associated one of said number of keys; wherein said keypad is further connected to said motor speed sensing means such that said predetermined motor speed is selectable by pressing one of said number of keys.

* * * * *